US009114200B2

(12) United States Patent
Constant et al.

(10) Patent No.: US 9,114,200 B2
(45) Date of Patent: *Aug. 25, 2015

(54) INJECTABLE HYDROGEL FILAMENTS FOR BIOMEDICAL USES

(75) Inventors: Michael J. Constant, Mission Viejo, CA (US); Gregory M. Cruise, Rancho Santa Margarita, CA (US); E. Michael Keeley, Huntington Beach, CA (US); Alejandro Berenstein, New York, NY (US)

(73) Assignee: MicroVention, Inc., Tustin, CA (US)

( * ) Notice: Subject to any disclaimer, the term of this patent is extended or adjusted under 35 U.S.C. 154(b) by 199 days.

This patent is subject to a terminal disclaimer.

(21) Appl. No.: 12/890,540

(22) Filed: Sep. 24, 2010

(65) Prior Publication Data

US 2011/0212178 A1 Sep. 1, 2011

Related U.S. Application Data

(60) Provisional application No. 61/363,978, filed on Jul. 13, 2010, provisional application No. 61/245,613, filed on Sep. 24, 2009.

(51) Int. Cl.
*A61F 2/00* (2006.01)
*A61F 13/00* (2006.01)
*A61L 31/18* (2006.01)
*A61L 31/16* (2006.01)
*A61L 31/06* (2006.01)
*A61L 31/14* (2006.01)

(52) U.S. Cl.
CPC ............... *A61L 31/18* (2013.01); *A61L 31/06* (2013.01); *A61L 31/145* (2013.01); *A61L 31/16* (2013.01); *A61L 2400/06* (2013.01)

(58) Field of Classification Search
None
See application file for complete search history.

(56) References Cited

U.S. PATENT DOCUMENTS

| | | |
|---|---|---|
| 3,709,842 A | 1/1973 | Stoy et al. |
| 3,749,085 A | 7/1973 | Willson et al. |
| 4,020,829 A | 5/1977 | Willson et al. |
| 4,301,803 A | 11/1981 | Handa et al. |
| 4,304,232 A | 12/1981 | Michaels |
| 4,365,621 A | 12/1982 | Brundin |
| 4,402,319 A | 9/1983 | Handa et al. |
| 4,493,329 A | 1/1985 | Crawford et al. |
| 4,509,504 A | 4/1985 | Brundin |
| 4,529,739 A | 7/1985 | Scott et al. |
| 4,551,132 A | 11/1985 | Pasztor et al. |
| 4,663,358 A | 5/1987 | Hyon et al. |
| 4,795,741 A | 1/1989 | Leshchiner et al. |
| 4,819,637 A | 4/1989 | Dormandy, Jr. et al. |
| 4,932,419 A | 6/1990 | de Toledo |
| 4,951,677 A | 8/1990 | Crowley et al. |
| 4,994,069 A | 2/1991 | Ritchart et al. |
| 5,120,349 A | 6/1992 | Stewart et al. |
| 5,122,136 A | 6/1992 | Guglielmi et al. |
| 5,129,180 A | 7/1992 | Stewart |
| 5,133,731 A | 7/1992 | Butler et al. |
| 5,147,646 A | 9/1992 | Graham |
| 5,154,705 A | 10/1992 | Fleischhacker et al. |
| 5,163,952 A | 11/1992 | Froix |
| 5,165,421 A | 11/1992 | Fleischhacker et al. |
| 5,217,484 A | 6/1993 | Marks |
| 5,226,911 A | 7/1993 | Chee et al. |
| 5,258,042 A | 11/1993 | Mehta |
| 5,304,194 A | 4/1994 | Chee et al. |
| 5,312,415 A | 5/1994 | Palermo |
| 5,350,397 A | 9/1994 | Palermo et al. |
| 5,354,290 A | 10/1994 | Gross |
| 5,373,619 A | 12/1994 | Fleischhacker et al. |
| 5,382,259 A | 1/1995 | Phelps et al. |
| 5,382,260 A | 1/1995 | Dormandy, Jr. et al. |
| 5,443,478 A | 8/1995 | Purdy |
| 5,449,369 A | 9/1995 | Imran |
| 5,456,693 A | 10/1995 | Conston et al. |
| 5,469,867 A | 11/1995 | Schmitt |
| 5,476,472 A | 12/1995 | Dormandy, Jr. et al. |
| 5,483,022 A | 1/1996 | Mar |
| 5,522,822 A | 6/1996 | Phelps et al. |

(Continued)

FOREIGN PATENT DOCUMENTS

| | | |
|---|---|---|
| EP | 809519 B1 | 12/1997 |
| WO | 91/16057 A | 10/1991 |

(Continued)

OTHER PUBLICATIONS

WIPO, U.S. International Search Authority, International Search Report and Written Opinion mailed Nov. 30, 2010 in International Patent Application No. PCT/US2010/050296, 8 pages.
Ahuja et al., Platinum coil coatings to increase thrombogenicity: a preliminary study in rabbits, AJNR, 14: 794-789 (1993).
Almany, Biomaterials, 26, 2005, 2467-2477, Biosynthetic hydrogel scaffolds made from fibrinogen and polyethylene glycol for 3D cell cultures.
Carelli V. et al., "Silicone microspheres for pH-controlled gastrointestinal drug delivery," 1999, International Journal of Pharmaceutics, V179, p. 73-83.
Chirila et al., Poly(2-hydroxyethyl metharcrylate) sponges ans implant materials: in vivo and in vitro evaluation of cellular invasion. Biomaterials, 14(1):26-38 (1993).
Constant et al., Preparation, Characterization, and Evaluation of Radiopaque Hydrogel Filaments for Endovascular Embolization. Journal of Biomedical Materials Research Part B: Applied Biomaterials, vol. 89B, No. 2, pp. 306-313 (2008).
Edleman et al., Controlled and modulated release of basic fibroblast growth factor. Biomaterials, vol. 12, pp. 619-626 (1991).

(Continued)

*Primary Examiner* — Susan Tran
(74) *Attorney, Agent, or Firm* — K&L Gates LLP; Louis C. Cullman; Brian J. Novak

(57) ABSTRACT

Described herein are apparatus, compositions, systems and associated methods to occlude structures and malformations with radiopaque hydrogel filaments with delayed controlled rates of expansion permitting the repositioning of the device once inside the structure or malformation. Further described is a device for implantation in an animal comprising a difunctional, low molecular weight ethylenically unsaturated shapeable macromer; an ethylenically unsaturated monomer; and a radiopaque element, wherein said device contains no support members. Methods of forming such devices are also disclosed.

44 Claims, 3 Drawing Sheets

(56) References Cited

U.S. PATENT DOCUMENTS

| | | |
|---|---|---|
| 5,525,334 A | 6/1996 | Ito et al. |
| 5,536,274 A | 7/1996 | Neuss |
| 5,541,234 A | 7/1996 | Unger et al. |
| 5,573,520 A | 11/1996 | Schwartz et al. |
| 5,573,994 A | 11/1996 | Kabra et al. |
| 5,578,074 A | 11/1996 | Mirigian |
| 5,580,568 A | 12/1996 | Greff et al. |
| 5,582,610 A | 12/1996 | Grossi et al. |
| 5,582,619 A | 12/1996 | Ken |
| 5,607,417 A | 3/1997 | Batich et al. |
| 5,609,629 A | 3/1997 | Fearnot et al. |
| 5,612,050 A | 3/1997 | Rowe et al. |
| 5,624,461 A | 4/1997 | Mariant |
| 5,624,685 A | 4/1997 | Takahashi et al. |
| 5,634,936 A | 6/1997 | Linden et al. |
| 5,645,558 A | 7/1997 | Horton |
| 5,651,979 A | 7/1997 | Ron et al. |
| 5,658,308 A | 8/1997 | Snyder |
| 5,672,634 A | 9/1997 | Tseng et al. |
| 5,678,296 A | 10/1997 | Fleischhacker et al. |
| 5,690,666 A | 11/1997 | Berenstein et al. |
| 5,690,667 A | 11/1997 | Gia |
| 5,690,671 A | 11/1997 | McGurk et al. |
| 5,718,711 A | 2/1998 | Berenstein et al. |
| 5,725,568 A | 3/1998 | Hastings |
| 5,749,894 A | 5/1998 | Engelson |
| 5,750,585 A | 5/1998 | Park et al. |
| 5,752,974 A | 5/1998 | Rhee et al. |
| 5,766,160 A | 6/1998 | Samson et al. |
| 5,766,219 A | 6/1998 | Horton |
| 5,823,198 A | 10/1998 | Jones et al. |
| 5,853,418 A | 12/1998 | Ken et al. |
| 5,883,705 A | 3/1999 | Minne et al. |
| 5,891,155 A | 4/1999 | Irie |
| 5,952,232 A | 9/1999 | Rothman |
| 5,976,162 A | 11/1999 | Doan et al. |
| 5,980,514 A | 11/1999 | Kupiecki et al. |
| 6,004,338 A | 12/1999 | Ken et al. |
| 6,013,084 A | 1/2000 | Ken et al. |
| 6,015,424 A | 1/2000 | Rosenbluth et al. |
| 6,063,100 A | 5/2000 | Diaz et al. |
| 6,066,149 A | 5/2000 | Samson et al. |
| 6,093,199 A | 7/2000 | Brown et al. |
| 6,096,034 A | 8/2000 | Kupiecki et al. |
| 6,103,865 A | 8/2000 | Bae et al. |
| 6,136,015 A | 10/2000 | Kurz et al. |
| 6,159,165 A | 12/2000 | Ferrera et al. |
| 6,168,570 B1 | 1/2001 | Ferrera |
| 6,171,326 B1 | 1/2001 | Ferrera et al. |
| 6,179,857 B1 | 1/2001 | Diaz et al. |
| 6,193,728 B1 | 2/2001 | Ken et al. |
| 6,201,065 B1 | 3/2001 | Pathak et al. |
| 6,231,590 B1 | 5/2001 | Slaikeu et al. |
| 6,238,403 B1 | 5/2001 | Greene, Jr. et al. |
| 6,245,090 B1 | 6/2001 | Gilson et al. |
| 6,270,748 B1 | 8/2001 | Annan et al. |
| 6,280,457 B1 | 8/2001 | Wallace et al. |
| 6,287,318 B1 | 9/2001 | Villar et al. |
| 6,299,604 B1 | 10/2001 | Ragheb et al. |
| 6,299,619 B1 | 10/2001 | Greene, Jr. et al. |
| 6,299,627 B1 | 10/2001 | Eder et al. |
| 6,312,421 B1 | 11/2001 | Boock |
| 6,399,886 B1 | 6/2002 | Avellanet |
| 6,423,085 B1 | 7/2002 | Murayama et al. |
| 6,425,893 B1 | 7/2002 | Guglielmi |
| 6,537,569 B2 | 3/2003 | Cruise et al. |
| 6,602,261 B2 | 8/2003 | Greene, Jr. et al. |
| 6,605,294 B2 | 8/2003 | Sawhney |
| 6,623,450 B1 | 9/2003 | Dutta |
| 6,634,361 B1 | 10/2003 | Nikolchev et al. |
| 6,684,884 B2 | 2/2004 | Nikolchev et al. |
| 6,723,108 B1 | 4/2004 | Jones et al. |
| 6,849,081 B2 | 2/2005 | Sepetka et al. |
| 6,860,893 B2 | 3/2005 | Wallace et al. |
| 6,878,384 B2 | 4/2005 | Cruise et al. |
| 6,887,974 B2 | 5/2005 | Pathak |
| 7,033,374 B2 | 4/2006 | Schaefer et al. |
| 7,066,904 B2 | 6/2006 | Rosenthal et al. |
| 7,070,607 B2 | 7/2006 | Murayama et al. |
| 2001/0023325 A1 | 9/2001 | Ferrera |
| 2002/0169473 A1 | 11/2002 | Sepetka et al. |
| 2002/0176880 A1 | 11/2002 | Cruise et al. |
| 2003/0134032 A1 | 7/2003 | Chaouk |
| 2003/0220245 A1 | 11/2003 | Hubbell et al. |
| 2003/0232895 A1 | 12/2003 | Omidian et al. |
| 2004/0006354 A1 | 1/2004 | Schaefer et al. |
| 2004/0059370 A1 | 3/2004 | Greene et al. |
| 2004/0098028 A1 | 5/2004 | Martinez |
| 2005/0119687 A1 | 6/2005 | Dacey et al. |
| 2005/0171572 A1 | 8/2005 | Martinez |
| 2005/0196426 A1 | 9/2005 | Cruise et al. |
| 2006/0052815 A1 | 3/2006 | Fitz et al. |
| 2006/0074370 A1 | 4/2006 | Zhou |
| 2007/0202046 A1* | 8/2007 | Dave ............................ 424/9.41 |
| 2007/0288084 A1* | 12/2007 | Lee et al. ..................... 623/1.16 |
| 2007/0299464 A1* | 12/2007 | Cruise et al. ................. 606/192 |
| 2008/0208167 A1 | 8/2008 | Stankus |
| 2009/0164013 A1* | 6/2009 | Cruise et al. ............... 623/11.11 |
| 2009/0232869 A1 | 9/2009 | Greene |
| 2010/0241160 A1 | 9/2010 | Murphy |
| 2011/0184455 A1 | 7/2011 | Keeley |
| 2012/0283769 A1 | 11/2012 | Cruise et al. |
| 2012/0289995 A1 | 11/2012 | Constant et al. |
| 2013/0131716 A1 | 5/2013 | Cruise et al. |

FOREIGN PATENT DOCUMENTS

| | | |
|---|---|---|
| WO | 94/03155 A1 | 2/1994 |
| WO | 97/22365 A1 | 6/1997 |
| WO | 97/26939 A1 | 7/1997 |
| WO | 97/27888 A1 | 8/1997 |
| WO | 98/01421 A1 | 1/1998 |
| WO | 98/43615 A1 | 10/1998 |
| WO | 99/23954 A1 | 5/1999 |
| WO | 99/44538 A1 | 9/1999 |
| WO | 99/56783 A1 | 11/1999 |
| WO | 99/65401 A1 | 12/1999 |
| WO | 00/27445 A1 | 5/2000 |
| WO | 00/38651 A1 | 7/2000 |
| WO | 00/74577 A1 | 12/2000 |
| WO | 01/68720 A1 | 9/2001 |
| WO | 02/05731 A1 | 1/2002 |
| WO | 02/096302 A1 | 12/2002 |
| WO | 03/043552 A1 | 5/2003 |
| WO | 2005/032337 A2 | 4/2005 |
| WO | 2007/147145 A2 | 12/2007 |
| WO | 2009/086208 A2 | 7/2009 |
| WO | 2011/038291 A1 | 3/2011 |
| WO | 2011/053555 A1 | 5/2011 |
| WO | 2012/145431 A3 | 10/2012 |

OTHER PUBLICATIONS

European Search Opinion for EP Application No. 10819570 mailed Mar. 31, 2014.
European Search Opinion for EP Application No. 10827370 mailed Apr. 1, 2014.
Graves et al., Endovascular occlusion of the carotid or vertebral artery with temporary proximal flow arrest and mircocoils: clinical results. AJNR Am. J. Neuroradiol., vol. 18, pp. 1201-1206 (1997).
Hoekstra, D., Hyaluronan-modified surfaces for medical devices. Medical Device & Diagnostic Industry, pp. 48-56 (1999).
Hogg et al., Interaction of platelet-derived growth factor with thrombospondin 1. Biochem. J. 326, pp. 709-716 (1997).
Horak et al., Hydrogels in endovascular embolization. II. Clinical use of spherical particles. Biomaterials , 7(6): 467-470 (1986).
Horak et al., New radiopaque polyHEMA-based hydrogel particles. J. Biomed. Matter Res., 34(2): 183-188 (1997).
Huang, et al., "Synthesis and Characterization of Self-Assembling Block Copolymers Containing Adhesive Molecules," Polymer Preprints, vol. 42, No. 2, 2001, pp. 147-148.
International Search Report mailed on Dec. 17, 2010 for International Patent Application No. PCT/US2010/053972.

(56) References Cited

OTHER PUBLICATIONS

International Search Report mailed on Feb. 5, 2009 for International Patent Application No. PCT/US2007/071395.

Kim, Drug release from pH-sensitive interpenetrating polymer networks hydrogel based on poly (ethylene glycol) Macromer and Poly (acrylic acid) prepared by UV Cured Method, ArchPharmRes, vol. 19(1), 1996, p. 18-22.

Klier, Self Associating Networks of Poly(methacrylic acid g-ethylene glycol) Marcomolecules 1990, vol. 23, 1990, p. 4944-4949.

Larsen et al., Hylan gel composition for percutaneous embolization. Journal of Biomedical Materials Research, vol. 25, Issue 6, pp. 699-710 (1991).

Latchaw et al., Polyvinyl foam embolization of vascular and neoplastic lesions of the head, neck, and spine. Radiology, 131: 669-679 (1979).

Li, Jian et al., Preparation of PEG/Aac copolymerric hydrogel and study of pH-sensitivity. Chemistry World, Issue 1, pp. 20-23 (2005).

Mellott, Michael B. et al., Release of protein from highly cross-linked hydrogels of poly(ethylene glycol) diacrylate fabricated by UV polymerization. Biomaterials, 22(2001) 929-941.

Murayama et al., Cellular responses of bioabsorbable polymeric material and guglielmi detachable coil in experimental aneurysms. Stroke, pp. 1120-1128 (2002).

Persidis, A., Tissue engineering. Nature Biotechnology, 17, pp. 508-510 (1999).

Schmutz et al., Embolization of cerebral arteriovenous malformations with silk: histopathologic changes and hemorrhagic complications. AJNR Am. J. Neuroradiol., vol. 18, pp. 1233-1237 (1997).

Schoenmakers, The effect of the linker on the hydrolysis rate of drug-linked ester bonds, J. Cont. Rel., 95, 2004, pp. 291-300.

Supplementary European Search Report for EP Application No. 10819570 mailed Mar. 31, 2014.

Supplementary European Search Report for EP Application No. 10827370 mailed Apr. 1, 2014.

Vinuela et al., Guglielmi detachable coil embolization of acute intracranial aneurysm: perioperative anatomical and clinical outcome in 403 patients. J. Neurosurg., vol. 86, pp. 475-482 (1997).

Woerly et al., Intracerebral implantation of hydrogel-coupled adhesion peptides: tissue reaction. Journal of Neural Transplantation & Plasticity, vol. 5, No. 4, pp. 245-255 (1995).

Zollikofer et al., A combination of stainless steel coil and compressed ivalon: a new technique for embolization of larger arteries and arteriovenous fistulas. Radiology, 138: 229-231 (1981).

Zollikofer et al., Therapeutic blockade of arteries using compressed invalon. Radiology, 136: 635-640 (1980).

\* cited by examiner

INJECTABLE HYDROGEL FILAMENTS FOR BIOMEDICAL USES

RELATED APPLICATIONS

This application claims priority to U.S. Provisional Application Ser. No. 61/363,978 filed Jul. 13, 2010 entitled Injectable Hydrogel Filaments for Biomedical Uses, and U.S. Provisional Application Ser. No. 61/245,613 filed Sep. 24, 2009 entitled Injectable Hydrogel Filaments for Biomedical Uses both of which are hereby incorporated herein by reference.

FIELD OF THE INVENTION

The present invention relates generally to medical treatment apparatus and methods, more particularly, extremely flexible injectable hydrogel filaments visible under x-ray fluoroscopy and optionally magnetic resonance imaging, and methods for use of such materials in biomedical treatment.

BACKGROUND OF THE INVENTION

Presently, for patients suffering from cerebral and/or peripheral vascular disease in extremely distal vessels, such as aneurysms, fistulae or arterio-venous malformations (AVM's), an interventional neuroradiologist/neurosurgeon has a variety of embolic choices: polymer beads, polyvinyl alcohol foam particles, cyanoacrylate glue, injectable polymeric liquids, and soft injectable platinum coils. All these types of embolic agents have advantages and disadvantages associated with them. Polymer beads and foam particles are easily injected down flow directed microcatheters but generally are not visible under x-ray fluoroscopy. Cyanoacrylate glue and polymeric liquids often provide sufficient occlusion but at a risk of adhering sections of the microcatheter permanently inside the vasculature. Soft injectable platinum coils, described in U.S. Pat. No. 5,690,666, to Berenstein et al., are easy to deploy and provide durable occlusion but are not visible under magnetic resonance imaging (MRI) and do not permit the use of computed tomography angiography (CT) for patient follow up.

Despite these embolic choices, there exists an unmet clinical need for safe, extremely flexible, injectable embolic devices that deploy easily through flow directed micro catheters into the distal vasculature, resulting in durable vessel occlusion, visible under x-ray fluoroscopy, MRI and allows for CT follow up.

SUMMARY OF THE INVENTION

Described herein are apparatuses, compositions, systems and associated methods to occlude structures and malformations in body lumens with flexible, injectable hydrogel filaments with delayed controlled rates of expansion including one or more visualization agents. The structures and malformations can be a result of any number of cerebral and/or peripheral diseases. Generally, the controlled rate of expansion is imparted through the incorporation of ethylenically unsaturated monomers with ionizable functional groups, (e.g. amines, carboxylic acids). For example, if acrylic acid is incorporated into the cross-linked polymeric network the hydrogel can be introduced through a microcatheter filled with blood or saline at physiological pH and will not fully expand until the carboxylic acid groups deprotonate. Conversely, if an amine-containing monomer is incorporated into the cross-linked network the hydrogel can be introduced through a microcatheter filled with blood or saline at physiological pH and will not fully expand until the amine groups protonate.

In one embodiment described herein is a device for implantation comprising a difunctional, low molecular weight ethylenically unsaturated shapeable macromer; an ethylenically unsaturated monomer; and a visualization agent, wherein the device contains no metallic support members. The device can have a flexibility or stiffness that facilitates injection though a syringe with pressurized fluid to distal locations in the body. Preferably, the device has a bending resistance between 0.5 and 0.1 mg on a sample length of one inch and more preferably has a bending resistance of 0.3 mg (as measured on a Gurley 4171 ET tubular sample stiffness tester with a 5 g counterweight attached to its measuring vein).

In one embodiment, the macromer has a molecular weight of about 100 grams/mole to about 5000 grams/mole. In another embodiment, the hydrogel is environmentally-responsive. In yet another embodiment, the ethylenically unsaturated monomer comprises one or more ionizable functional groups.

In one embodiment, the macromer comprises poly(tetramethylene oxide) diacrylamide, polyethylene glycol, propylene glycol, poly(ethylene glycol) diacrylamide, poly(ethylene glycol) diacrylate, poly(ethylene glycol) dimethacrylate, derivatives thereof, or combinations thereof. In another embodiment, the ethylenically unsaturated monomer comprises N,N'-methylenebisacrylamide, N-vinyl pyrrolidinone, 2-hydroxyethyl methacrylate, derivatives thereof, or combinations thereof.

In one embodiment, the visualization agents include radiopaque element comprises of barium, tantalum, platinum, gold, or combinations thereof. In one embodiment, the visualization agent comprises gadolinium or super paramagnetic iron oxide to impart visibility under magnetic resonance imaging.

In one embodiment, the visualization agent is barium sulfate. In one embodiment, the percentage of barium sulfate used is between 35-55%. In a first preferred embodiment, the component percentage of barium sulfate used is 45.1%. In a second preferred embodiment, the component percentage of barium sulfate used is 48.6%.

In one embodiment, the prepolymer solution is mixed with a homogenizer to evenly disperse the visualization agent resulting in a more consistent particle distribution, facilitating injection into small diameter tubes and strengthening the resulting polymer.

In one embodiment, the polymerization of the macromer and the monomer is initiated by azobisisobutyronitrile, N,N, N',N'-tetramethylethylenediamine, ammonium persulfate, benzoyl peroxides, 2,2'-azobis(2-methylpropionamidine) dihydrochloride, derivatives thereof, or combinations thereof.

In another embodiment, the hydrogel is substantially non-bioresorbable. In another embodiment, the hydrogel is bioresorbable.

One embodiment described herein is a method for preparing a device for implantation in an animal comprising: combining a difunctional, low molecular weight ethylenically unsaturated shapeable macromer; an ethylenically unsaturated monomer; a visualization agent, and a solvent to prepare a prepolymer solution.

In one embodiment of the method, the solvent comprises isopropyl alcohol, dichloromethane, acetone, water, ethanol, or combinations thereof. In another embodiment, the difunctional, low molecular weight ethylenically unsaturated shapeable macromer has a molecular weight of about 100 grams/ mole to about 5000 grams/mole. In yet another embodiment, the ethylenically unsaturated monomer comprises ionizable functional groups.

In one embodiment, the method further comprises the step of adding a second an ethylenically unsaturated monomer to the prepolymer solution.

In another embodiment, a device is described for implantation comprising: a difunctional, low molecular weight ethylenically unsaturated shapeable macromer with a molecular weight of about 100 grams/mole to about 5000 grams/mole; an ethylenically unsaturated monomer; and a visualization agent, wherein the device contains no metallic support members.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Figure 1:
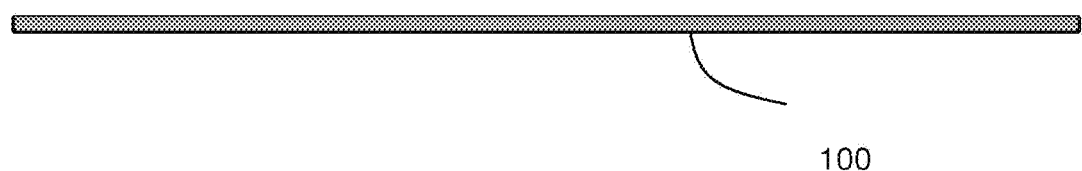
FIG. 1 illustrates a preferred embodiment of a hydrogel filament according to the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Described herein are apparatuses, compositions, systems and associated methods for occluding structures and malformations resulting from one or more cerebral and/or peripheral vascular diseases. Hydrogel filaments comprising one or more visualization agents having delayed, controlled rates of expansion are used to treat these structures and malformations. Further, the hydrogel filaments including one or more visualization agents, for example radiopaque elements or fillers, with controlled rates of expansion give a surgeon a sufficient amount of time to deliver the hydrogel through a microcatheter filled with blood or saline at physiological pH without the need to rush as a result of immediate filament expansion.

Figure 2:
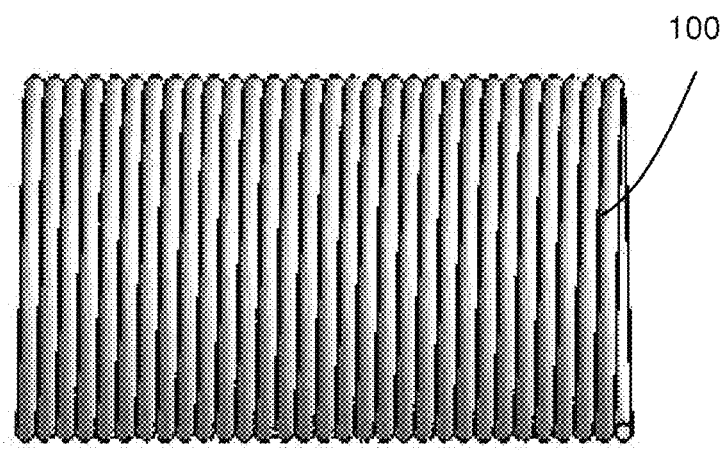
FIG. 2 illustrates the hydrogel filament of FIG. 1 in a helical configuration.

Turning to FIG. 1, a preferred embodiment of a hydrogel filament 100 in a dried state is illustrated in a straight configuration. Preferably, the hydrogel filament 100 has a length between about 0.5 cm and about 100 cm and has a diameter between about 0.008 inches and about 0.100 inches. Once delivered to the chosen intravascular site, the Hydrogel filament 100 can form a memory-set, three-dimensional shape, such as the helical shape shown in FIG. 2. However, it should be understood that a variety of different shapes are possible, such as a tornado shape, multiple adjacent coils and similar complex arrangements.

Figure 3:
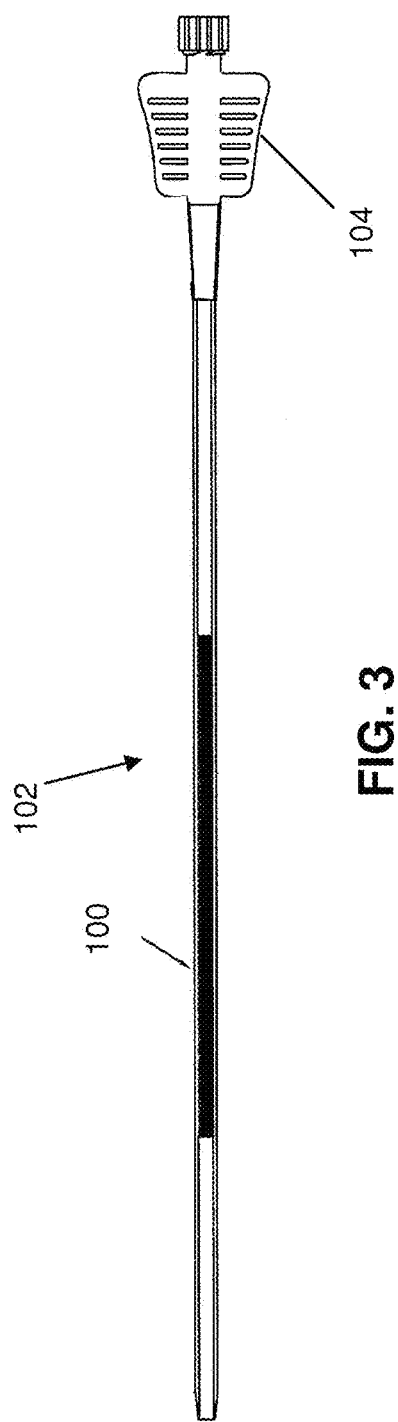
FIG. 3 illustrates the hydrogel filament of FIG. 1 in an introducer according to the present invention; and, FIG. 4 illustrates the hydrogel filament of FIG. 1 being delivered via a microcatheter.

As seen in FIG. 3, the dried hydrogel filament 100 is positioned within an introducer 102 prior to use in a treatment procedure. Preferably, both the introducer 102 and the hydrogel filament 100 can be sterilized and packaged for use at a later date.

Figure 4:
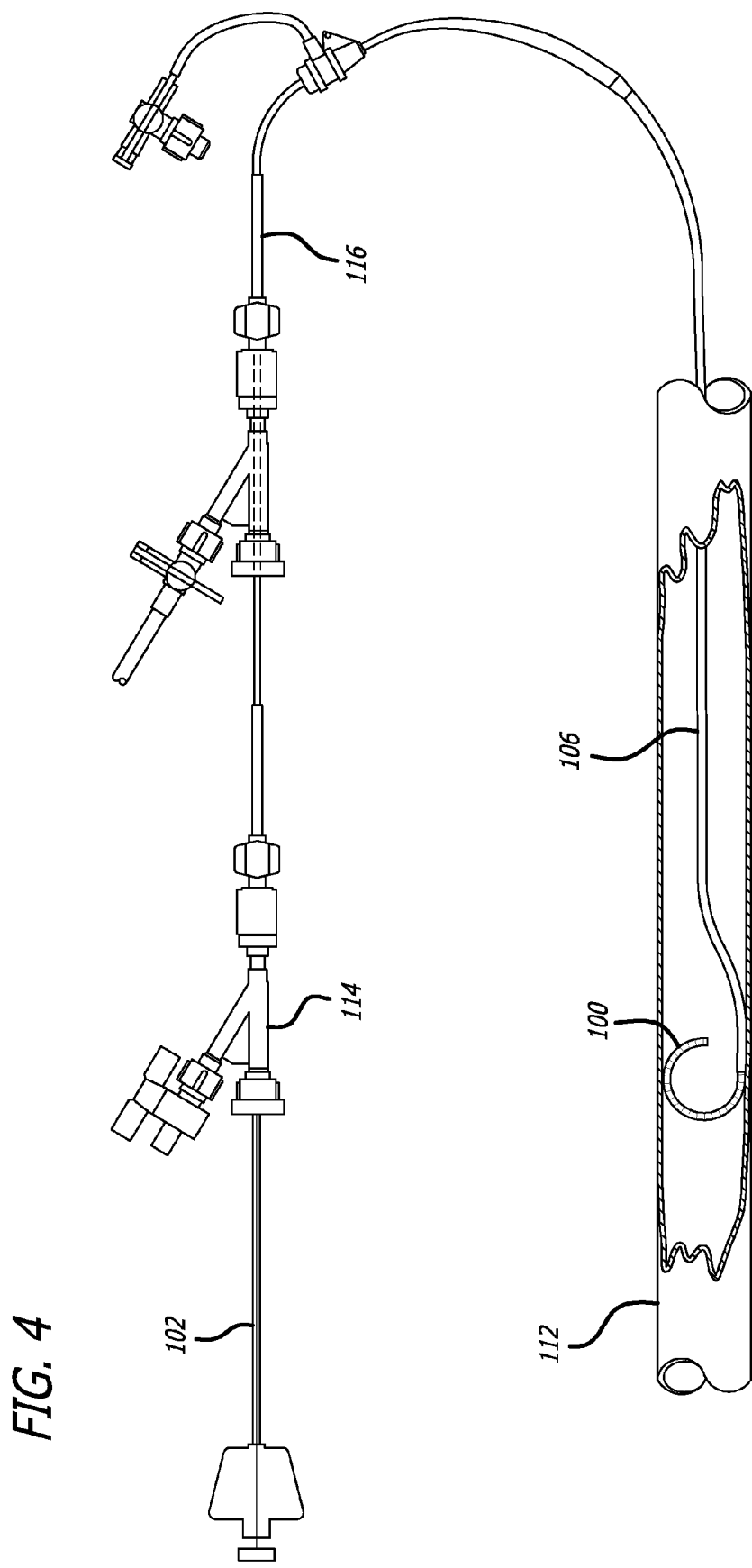

When the user is ready to begin the procedure, a delivery system is used to deliver the hydrogel filament. FIG. 4 illustrates an example delivery system, including a rotating hemostatic valve 114, a guide catheter 116, and a microcatheter 106.

The microcatheter 106 is advanced with in a vessel 112 of a patient until a distal end of the microcatheter 106 is located at the target location within the vessel 112. Next, a distal end of the introducer 102 is connected to the delivery system and an introducer hub 104 is connected to a syringe (not shown). Preferably the syringe contains saline or other physiological solution compatible for use within a patient.

The syringe delivers pressurized solution within introducer 102 so as to advance the hydrogel filament 100 out of the introducer 102 and into the microcatheter 106. Once the hydrogel filament 100 has completely entered the microcatheter 106, the introducer 102 can be removed from the proximal end of the microcatheter 106 and replaced with a syringe containing additional physiological solution.

When the user is ready to deliver the hydrogel filament 100, the syringe is depressed, causing the physiological solution to pressurize within the microcatheter 106 and push the hydrogel filament 100 into the vessel 112, as seen in FIG. 4. Preferably, the hydrogel filament 100 then begins a controlled rate of expansion at the target area.

Generally, the controlled rate of expansion of the hydrogel filaments is imparted through the incorporation of ethylenically unsaturated monomers with ionizable functional groups, (e.g. acidic or basic groups). For example, if acrylic acid is incorporated into the cross-linked polymeric network the hydrogel can be introduced through a microcatheter filled with blood or saline at physiological pH. The hydrogel cannot and will not expand until the carboxylic acid groups deprotonate. Conversely, if a basic, amine containing monomer is incorporated into the cross-linked network, the hydrogel can be introduced through a microcatheter filled with blood or saline at physiological pH. The hydrogel cannot and will not fully expand until the amine groups are protonated.

In one embodiment, whether acidic or basic groups are utilized on the monomeric species according to the present description, the devices described herein are expansible at physiological conditions. Physiological condition as used herein means a condition having at least one environmental characteristic found within or on the human body. Such characteristics include isotonic environment, pH buffered environment, aqueous environment, a pH of about 7, or combinations thereof and can be found in, for example, an isotonic solution, water, blood, spinal fluid, plasma, serum, vitreous humor or urine.

In one embodiment generally described herein are devices for implantation comprising a difunctional, low molecular weight ethylenically unsaturated shapeable macromer; an ethylenically unsaturated monomer; and a visualization element, wherein the device contains no support members.

Further, the absence of metallic support members from the devices described herein allow for better resolution under various imaging procedures. Metallic support members, for example, can distort the imaging of a device by producing flares from the metallic support members within the image. As such, providing a device with no metallic support members, but including one or more visualization agents, such as radiopaque elements or fillers, as taught herein allows one skilled in the art to attain a more precise and accurate image of the device both during and after implantation. Such devices with no metallic support members may include support members not visible to imaging techniques, for example polymeric support members.

In another embodiment described herein is a method for preparing a device for implantation in an animal comprising the steps of combining a difunctional, low molecular weight ethylenically unsaturated shapeable macromer; an ethylenically unsaturated monomer; a visualization element, and a solvent to prepare a prepolymer solution; and treating the prepolymer solution to prepare hydrogel that is expansible at physiological conditions.

Generally, the prepolymer solution is comprised of a solvent, a difunctional ethylenically unsaturated macromer, optional ethylenically unsaturated monomer or monomers, optional cross-linkers, and one or more visualization agents, such as radiopaque elements or fillers, which include, but are not limited to, barium, tantalum, platinum, and gold.

The solvent in the prepolymer solution serves to completely dissolve of all of the macromers and monomers within the prepolymer solution. If a liquid monomer (e.g. 2-hydroxyethyl methacrylate) is used, a solvent may not be necessary. The solvent, if necessary, is selected based on the solubility of the macromers and monomers. Preferred solvents are isopropyl alcohol (IPA, isopropanol), ethanol, water, dichloromethane, and acetone; however, a number of other solvents could be utilized and are know to those skilled in the art. Preferred solvent concentrations range from about 10% w/w to about 50% w/w of the prepolymer solution. In one preferred embodiment, the solvent concentration is about 20% w/w of the prepolymer solution.

The difunctional low molecular weight ethylenically unsaturated shapeable macromer serves to cross-link the polymer chains during polymerization and impart flexibility to the resulting polymer. Such macromers include two ethylenically unsaturated groups. In one embodiment, the macromers described herein have a low molecular weight. The macromers described herein have a molecular weight ranging from about 100 g/mol to about 5,000 g/mole, or about 200 g/mole to about 2,500 g/mole, more preferably about 400 g/mole to about 1,000 g/mole. A preferred macromer is poly(tetramethylene oxide) diacrylamide because of its relative tensile strength and ability to hold a shape. If degradation of the resulting polymer is desired, a preferred macromer is poly(tetramethylene oxide) diacrylate. Alternatively, other macromers such as the polyethers poly(propylene glycol) and poly(ethylene glycol) or derivatives of polyolefins such as poly(ethylene) are suitable.

"Ethylenically unsaturated" as used herein generally describes a compound with a group such as, but not limited to, vinyl, acrylate, methacrylate, or acrylamide groups including derivatives thereof or combinations thereof.

A "shapeable" macromer is used herein to describe the relative rigidity of the macromer and its ability to hold a particular shape. For example, a shapeable macromer according to the present description can be formed using a device such as a mandrel and can hold the resulting shape for implantation.

"Visualization agent" as used herein refers to any element that is added to or encompassed within the devices described herein that impart a means of visualizing the device either during or after implantation. Methods of visualization include, but are not limited to, x-rays, ultrasound, fluoroscopy, infrared radiation, ultraviolet light methods, magnetic resonance and combinations thereof. In one embodiment, the visualization agent can be one or more radiopaque elements or fillers which impart radiopacity to the devices described herein. In another embodiment, the visualization agent can be a non-radioapque element or filler such as gadolinium or iron oxide. Such non-radiopaque elements or fillers do not impart radiopacity to the devices described herein and can be imaged by, for example, magnetic resonance.

"Radiopaque" as used herein refers to elements or fillers as described above that impart radiopacity to the devices described herein and are detectable by a means of electrometric radiation such as, but not limited to, x-rays, ultrasound, fluoroscopy, infrared, ultraviolet and combinations thereof. In one embodiment, radiopaque elements described herein are detectable using x-rays or x-ray fluoroscopy.

The ionizable ethylenically unsaturated monomer serves to delay the expansion of the hydrogel filament, thereby establishing a controlled rate of expansion. In one embodiment, at least a portion, preferably about 1% to about 10% w/w of the monomer solution, more preferably about 1% to about 5% w/w of the prepolymer solution, of the monomers selected are ionizable. The preferred ionizable monomers may be acrylic acid or methacrylic acid. Derivatives and salts of both acids are also suitable ionizable components. Alternatively, in one embodiment, ionizable ethylenically unsaturated monomers are not utilized.

In one embodiment optional ethylenically unsaturated monomers are used to aid the polymerization process and can be any mono or multifunctional ethylenically unsaturated compound. In one embodiment, ethylenically unsaturated monomers with low molecular weights are preferred. Hydroxyethyl methacrylate (e.g. 2-hydroxyethyl acrylate), hydroxyethyl acrylate, N-vinyl pyrrolidinone and N, N'-methylenebisacrylamide are preferred ethylenically unsaturated monomers. Preferred concentrations of the ethylenically unsaturated monomers are less than about 15% w/w, more preferably about 10% w/w of the prepolymer solution.

In one preferred embodiment, the use of a multi-functional ethylenically unsaturated compound, such as N,N-methylenebisacrylamide can be used to further cross-link the polymer matrix. In another preferred embodiment, the preferred component percentage is in the range of up to 1%.

In one embodiment, the hydrogels and devices described herein further comprise visualization agents, such as, gadolinium or super paramagnetic iron oxide in addition to radiopaque elements to impart visibility of the devices under magnetic resonance imaging. In other embodiments, the gadolinium or super paramagnetic iron oxide are used instead of or in place of the radiopaque elements.

The prepolymer solution can be cross-linked by reduction-oxidation, radiation, heat, or any other method known in the art. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the prepolymer solution.

In a preferred embodiment, the cross-linking method utilizes azobisisobutyronitrile (AIBN) or another water soluble AIBN derivative (2,2'-azobis(2-methylpropionamidine) dihydrochloride). Other cross-linking agents useful according to the present description include N,N,N',N'-tetramethylethylenediamine, ammonium persulfate, benzoyl peroxides, and combinations thereof, including azobisisobutyronitriles. In one embodiment, the AIBN or derivative thereof is used at an elevated temperature.

After addition of AIBN, the prepolymer solution is injected into tubing with an inner diameter ranging from 0.010 inches to 0.075 inches and incubated for several hours in boiling water, i.e. 100° C. The immersion in boiling water allows for rapid heat transfer from the water to the prepolymer solution contained in the tubing. The selection of the tubing imparts microcatheter or catheter compatibility. For delivery through micro catheters, tubing diameters from about 0.010 inches to about 0.025 inches are preferred. In a preferred embodiment, the tubing is made from HYTREL® (DuPont, Wilmington, Del.). The HYTREL® tubing can be dissolved in solvents, facilitating removal of the polymer from the tubing.

In a preferred embodiment the prepolymer solution is mixed with a homogenizer prior to the addition of the AIBN.

If the tubing is wrapped around a mandrel prior to polymerization of the prepolymer solution, the resulting polymer will maintain the shape of the tubing, primarily as a result of the shapeable macromer within the prepolymer solution. Using this technique, helical, tornado, and complex shapes can be imparted to the polymer. The memory of the imparted shape is strongly influenced by the macromer selection. More hydrophobic macromers retain their imparted shape better than more hydrophilic macromers. It is preferred that an ethylenically unsaturated shapeable macromer be used in this embodiment.

In a preferred embodiment the inner diameter of the Hytrel tubing is formed with an oval shape. Once wrapped the inner diameter of the tubing will be drawn round as the tubing is compressed on the mandrel.

In one embodiment, the devices described herein are environmentally responsive. Environmentally responsive as used herein means that the devices change in some way in response to the surrounding environment. In one embodiment, this response to the surrounding environment is in the form of a controlled rate of expansion. A controlled rate of expansion of the hydrogels described herein is achieved through the protonation/deprotonation of ionizable functional groups present within or on the hydrogel network.

After the cross-linked hydrogel has been washed, it is dried to produce a dried hydrogel filament. The length can range from about 0.5 cm to about 100 cm and the diameter can range from about 0.008 inches to about 0.100 inches. To manufacture a fluid assisted injectable embolic device, a dried hydrogel filament is loaded into an introducer, packaged in a suitable pouch, and sterilized. Upon receipt, the surgeon injects saline through the introducer to remove air. The dried hydrogel filament is then injected into the microcatheter or catheter with a syringe filled with saline or other physiological solution. The saline or other physiological solution is used to assist in advancing the hydrogel filament down the catheter. The dried hydrogel filament is then advanced down the microcatheter or catheter to the embolization site with subsequent injections.

In other embodiments, the hydrogel is non-bioresorbable or substantially non-bioresorbable. A "non-bioresorbable" hydrogel as used herein is biocompatible and not subject to breakdown in vivo through the action of normal biochemical pathways. In one embodiment, the hydrogel is substantially non-bioresorbable and remains greater than 95% intact after 1 year of implantation. In other embodiments, the substantially non-bioresorbable hydrogel remains greater than 90% intact after 1 year.

In yet a further embodiment, the hydrogel is bioresorbable, meaning the hydrogel is biocompatible and is broken down in vivo through the action of normal biochemical pathways. In one embodiment, the hydrogel is bioresorbable and remains less than 5% intact after 1 year of implantation. In other embodiments, the hydrogel is bioresorbable and remains less than 5% intact after 2 years of implantation. In other embodiments, the hydrogel is bioresorbable and remains less than 5% intact after 5 years of implantation.

EXAMPLES

The following are non-limiting examples of some of the biomedical applications of hydrogels with visualization agents described herein. It will be appreciated, however, that this material has many other medical and non-medical applications in addition to the specific examples set forth herein.

Example 1

Preparation of PTMO 1000 Diacrylamide

First, 150 g of poly(tetramethylene oxide) (PTMO) 1000 was dried by azeotropic distillation with 1100 mL of toluene. Then, 50.2 mL of triethylamine was added with 27.9 mL of mesyl chloride and stirred for 4 hr. The solution was then filtered to remove salt and the solvent evaporated. The resulting product was added to 1000 ml of acetonitrile and 300 mL of 25% ammonia hydroxide and stirred for 3 days. The water was removed and the product dried by azeotropic distillation with toluene. The resulting dried PTMO diamine was dissolved in 1000 mL toluene. Then, 46.0 mL of triethylamine and 29.1 mL of acryloyl chloride were added and the reaction proceeded for 4 hr while stirring. The resulting solution was filtered and the solvent was removed leaving PTMO 1000 diacrylamide.

Example 2

Preparation of a Gd-DTPA Methacrylate Monomer

First, 2.74 g of gadolinium diethylenetriamine penta-acidic acid was dissolved in 95 mL of water along with 2.1 g of ethyl-3-(3-dimethylaminopropyl)-carbodiimide (EDC) and 1.65 g of aminoethylmethacrylate. The solution was adjusted to pH 8.0 and stirred for 5 hours. Once the reaction was complete, the solution was rotary evaporated under vacuum to remove the bulk of the water. The resulting product was placed in a vacuum oven and dried completely leaving gadolinium diethylenetriamine penta acidic acid methacrylate.

Example 3

Preparation of a 10-Sytem Flexible Barium Loaded Radiopaque Hydrogel Filament

To prepare a barium-loaded radiopaque hydrogel in an organic solvent, 0.625 g of acrylic acid, 6.25 g of poly(tetramethylene oxide) diacrylamide 1000, 1.56 g of 2-hydroxyethylmethacrylate, 265 mg of N,N-methylenebisacrylamide and 125 mg of azobis(2-methylpropionitrile) were dissolved in 4.38 mL of isopropyl alcohol. The solution was filtered through a 0.2 micron syringe filter. To 10.56 g of solution, 10 g of barium sulfate was added. This results in the following w/w component percentages: PTMO 24.3%, AIBN 0.5%, HEMA 6.1%, acrylic acid 2.4%, bisacrylamide 1.0%, isopropanol 17.0%, and barium sulfate 48.6%. The solution was homogenized using a Ultra-Turrax T-25 homogenizer. Once homogenized, the solution was sparged with argon for 10 min before injection into 0.010 inch HYTREL® tubing wrapped around a 4 mm mandrel using a ½ cc syringe. The tubes were heat sealed at both ends and placed in a 100° C. water bath for 1 hr, then overnight in an 80° C. oven to polymerize the solution. The resulting filament has a diameter when dry of 0.008 inches.

After drying and evaporation of the solvent, the weight percentages of the final implant are PTMO 30%, HEMA 7%, acrylic acid 3%, bisacrylamide 1%, and barium sulfate 59%.

Example 4

Preparation of an 18-Sytem Flexible Barium Loaded Radiopaque Hydrogel Filament

To prepare a barium-loaded radiopaque hydrogel in an organic solvent, 0.625 g of acrylic acid, 6.25 g of poly(tetramethylene oxide) diacrylamide 1000, 1.56 g of 2-hydroxyethylmethacrylate and 125 mg of azobis(2-methylpropionitrile) were dissolved in 4.38 mL of isopropyl alcohol. The solution was filtered through a 0.2 micron syringe filter. To 10.38 g of solution, 8.5 g of barium sulfate was added. This results in the following w/w component percentages: PTMO 26.5%, AIBN 0.5%, HEMA 6.6%, acrylic acid 2.7%, isopropanol 18.6%, and barium sulfate 45.1%. The solution was homogenized using a Ultra-Turrax T-25 homogenizer. Once homogenized, the solution was sparged with argon for 10 min before injection into 0.018 inch oval shaped HYTREL® tubing wrapped around a 4 mm mandrel using a 3 cc syringe. The tubes were heat sealed at both ends and placed in a 100° C. water bath for 1 hr, then overnight in an 80° C. oven to polymerize the solution. The resulting filament has a diameter when dry of 0.016 inches.

After drying and evaporation of the solvent, the weight percentages of the final implant are PTMO 33%, HEMA 8%, acrylic acid 3%, and barium sulfate 56%.

Example 5

Preparation of PEG 1000 Diacrylamide

First, 18 g of polyethylene glycol (PEG) 1000 was dried by azeotropic distillation with 200 mL of toluene. Then, 7.0 mL of triethylamine was added with 4.6 mL of mesyl chloride and stirred for 4 hr. The solution was then filtered to remove salt and the solvent evaporated. The resulting product was added to 150 mL of 25% ammonia hydroxide and stirred for 2 days. The water was removed and the product dried by azeotropic distillation with toluene. The resulting dried PEG diamine was dissolved in 20 mL dichloromethane and 50 mL toluene. Then, 7.0 mL of triethylamine and 4.9 mL of acryloyl chloride were added and the reaction proceeded for 4 hr while stirring. The resulting solution was filtered and the solvent was removed leaving PEG 1000 diacrylamide.

Example 6

Preparation of a Gd-DTPA Hydrogel Filament in Water

To prepare a Gd-DTPA hydrogel filament in water, 0.59 g of Gd-DTPA methacrylate, 0.25 g of acrylic acid, 5.25 g PEG diacrylamide 1000, 0.125 g methylenebisacrylamide, 6.0 g of barium sulfate, 0.5 g 2-hydroxyethylmethacrylate and 100 mg of 2,2'azobis(2-methylpropionamidine) dihydrochloride were dissolved in 2.5 mL of water. The solution was then sparged with argon for 10 min before injection into 0.020 inch HYTREL® tubing wrapped around a 4 mm mandrel using a 3 cc syringe. The tubes were heat sealed at both ends and placed in a 100° C. water bath for 1 hr, then overnight in an 80° C. oven to polymerize the solution.

Example 7

Preparation of a SPIO Hydrogel Filament in Water

To prepare a super paramagnetic iron oxide (SPIO) hydrogel filament in water, 0.953 mg of SPIO, 0.25 g of acrylic acid, 5.25 g PEG diacrylamide 1000, 0.125 g methylenebisacrylamide, 6.0 g of barium sulfate, 0.5 g 2-hydroxyethylmethacrylate and 100 mg of 2,2'azobis(2-methylpropionamidine) dihydrochloride were dissolved in 2.5 mL of water. The solution was then sparged with argon for 10 min before injection into 0.020 inch HYTREL® tubing wrapped around a 4 mm mandrel using a 3 cc syringe. The tubes were heat sealed at both ends and placed in a 100° C. water bath for 1 hr, then overnight in an 80° C. oven to polymerize the solution.

Example 8

Washing of a Radiopaque Hydrogel Filament

The hydrogel was removed by dissolving the tubing in a solution of 20% phenol in chloroform. After the tubing was dissolved, the phenol solution was exchanged with chloroform and washed for 1 hr. After 1 hr, the chloroform was exchanged and the hydrogel washed for another 1 hr. The chloroform was removed and the hydrogel dried in a vacuum oven for 2 hr at 50° C. To remove any unreacted monomers, the hydrogel was placed in ethanol for 12 hr. After 12 hr, the ethanol was exchanged and washed for 2 hr. After 2 hr, the ethanol was exchanged and the hydrogel washed for another 2 hr. The ethanol was removed and hydrogel dried in a vacuum oven for 12 hr.

Example 9

Measurement of Bending Resistance

The bending resistances of the unexpanded hydrogel samples were obtained using a Gurley 4171 ET tubular sample stiffness tester with a 5 g counterweight attached to its measuring vane. The sample length was one inch. The average result for three replicates is summarized in the following table.

| Sample | Measured Resistance (mg) |
| --- | --- |
| D-78 radiopaque hydrogel filament | 0.3 ± 0.2 |

The results demonstrate that the flexibility required for an injectable coil can be achieved with a radiopaque hydrogel filament.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facili-

What is claimed is:

1. A device for implantation comprising:
a filament including about 30% of a difunctional, low molecular weight ethylenically unsaturated shapeable poly(tetramethylene oxide) macromer; a first ethylenically unsaturated monomer, wherein said first monomer is ionizable; a second ethylenically unsaturated monomer; and a visualization agent,
wherein said device contains no support members and said filament has a bending resistance between about 0.5 mg and 0.1 mg.

2. The device according to claim 1 wherein said macromer has a molecular weight of about 100 grams/mole to about 5000 grams/mole.

3. The device according to claim 1 wherein said filament is environmentally-responsive.

4. The device according to claim 1 wherein said macromer comprises poly(tetramethylene oxide) diacrylate.

5. The device according to claim 1 wherein said first ethylenically unsaturated monomer comprises one or more ionizable functional groups.

6. The device according to claim 1 wherein said second ethylenically unsaturated monomer comprises N,N'-methylenebisacrylamide, N-vinyl pyrrolidinone, 2-hydroxyethyl methacrylate, derivatives thereof, or combinations thereof.

7. The device according to claim 1 wherein said macromer, said first monomer, and said second monomer are crosslinked with N,N,N',N'-tetramethylethylenediamine, ammonium persulfate, azobisisobutyronitrile, benzoyl peroxides, 2,2'-azobis(2-methylpropionamidine) dihydrochloride, derivatives thereof, or combinations thereof.

8. The device according to claim 1 wherein said visualization agent comprises 48.6% w/w barium sulfate.

9. The device according to claim 1 wherein said visualization agent comprises 45.1% w/w barium sulfate.

10. The device according to claim 1 wherein said visualization agent comprises 59% barium sulfate after drying.

11. The device according to claim 1 comprising about 7% hydroxyethyl methacrylate, about 3% acrylic acid, about 1% bisacrylamide, and about 59% barium sulfate after drying.

12. The device according to claim 1 wherein said visualization agent comprises 56% barium sulfate after drying.

13. The device according to claim 1 comprising about 8% hydroxyethyl methacrylate, about 3% acrylic acid, and about 56% barium sulfate after drying.

14. The device according to claim 1 wherein said visualization agent comprises gadolinium or iron oxide.

15. The device according to claim 1 wherein said visualization element comprise barium.

16. The device according to claim 7 wherein said crosslinker comprises N,N'-methylenebisacrylamide.

17. The device according to claim 5 wherein said ionizable functional groups comprise basic groups or acidic groups.

18. The device according to claim 17 wherein said basic groups comprise amine groups, derivatives thereof, or combinations thereof.

19. The device according to claim 17 wherein said acidic groups comprise a carboxylic acid, derivatives thereof, or combinations thereof.

20. The device according to claim 1 wherein said filament is substantially free of acrylamide.

21. The device according to claim 1 wherein said filament is substantially non-bioresorbable.

22. The device according to claim 1 wherein said filament is bioresorbable.

23. A device for implantation comprising:
a filament including about 33% of a difunctional, low molecular weight ethylenically unsaturated shapeable poly(tetramethylene oxide) macromer; a first ethylenically unsaturated monomer, wherein said first monomer is ionizable; a second ethylenically unsaturated monomer; and a visualization agent,
wherein said device contains no support members and said filament has a bending resistance between about 0.5 mg and 0.1 mg.

24. The device according to claim 23 wherein said macromer has a molecular weight of about 100 grams/mole to about 5000 grams/mole.

25. The device according to claim 23 wherein said filament is environmentally-responsive.

26. The device according to claim 23 wherein said macromer comprises poly(tetramethylene oxide) diacrylate.

27. The device according to claim 23 wherein said first ethylenically unsaturated monomer comprises one or more ionizable functional groups.

28. The device according to claim 23 wherein said second ethylenically unsaturated monomer comprises N,N'-methylenebisacrylamide, N-vinyl pyrrolidinone, 2-hydroxyethyl methacrylate, derivatives thereof, or combinations thereof.

29. The device according to claim 23 wherein said visualization agent comprises 48.6% w/w barium sulfate.

30. The device according to claim 23 wherein said visualization agent comprises 45.1% w/w barium sulfate.

31. The device according to claim 23 wherein said visualization agent comprises 59% barium sulfate after drying.

32. The device according to claim 23 comprising about 7% hydroxyethyl methacrylate, about 3% acrylic acid, about 1% bisacrylamide, and about 59% barium sulfate after drying.

33. The device according to claim 23 wherein said visualization agent comprises 56% barium sulfate after drying.

34. The device according to claim 23 comprising about 8% hydroxyethyl methacrylate, about 3% acrylic acid, and about 56% barium sulfate after drying.

35. The device according to claim 23 wherein said visualization agent comprises gadolinium or iron oxide.

36. The device according to claim 23 wherein said visualization element comprises barium.

37. The device according to claim 23 wherein said macromer, said first monomer, and said second monomer are crosslinked with N,N,N',N'-tetramethylethylenediamine, ammonium persulfate, azobisisobutyronitrile, benzoyl peroxides, 2,2'-azobis(2-methylpropionamidine) dihydrochloride, derivatives thereof, or combinations thereof.

38. The device according to claim 37 wherein said crosslinker comprises N,N'-methylenebisacrylamide.

39. The device according to claim 27 wherein said ionizable functional groups comprise basic groups or acidic groups.

40. The device according to claim 39 wherein said basic groups comprise amine groups, derivatives thereof, or combinations thereof.

41. The device according to claim 39 wherein said acidic groups comprise a carboxylic acid, derivatives thereof, or combinations thereof.

42. The device according to claim 23 wherein said filament is substantially free of acrylamide.

43. The device according to claim 23 wherein said filament is substantially non-bioresorbable.

44. The device according to claim 23 wherein said filament is bioresorbable.

* * * * *